United States Patent
Christini et al.

(10) Patent No.: US 6,915,156 B2
(45) Date of Patent: Jul. 5, 2005

(54) INTRACARDIAC DETECTION AND CONTROL OF REPOLARIZATION ALTERNANS

(75) Inventors: David J. Christini, Brooklyn, NY (US); Kenneth M. Stein, New York, NY (US); Bruce B. Lerman, New York, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 656 days.

(21) Appl. No.: 10/066,317

(22) Filed: Oct. 23, 2001

(65) Prior Publication Data

US 2002/0138106 A1 Sep. 26, 2002

Related U.S. Application Data

(60) Provisional application No. 60/242,652, filed on Oct. 23, 2000.

(51) Int. Cl.[7] .................................................. A61B 5/04
(52) U.S. Cl. ...................... 600/509; 600/516; 600/517; 607/2
(58) Field of Search ...................... 607/2, 25; 600/509, 600/516

(56) References Cited

U.S. PATENT DOCUMENTS

| | | | | |
|---|---|---|---|---|
| 4,802,491 A | | 2/1989 | Cohen et al. ............... | 128/702 |
| 5,148,812 A | * | 9/1992 | Verrier et al. .............. | 600/517 |
| 5,713,367 A | | 2/1998 | Arnold et al. .............. | 128/704 |
| 5,827,195 A | * | 10/1998 | Lander ....................... | 600/509 |
| 5,836,974 A | | 11/1998 | Christini et al. ............. | 607/5 |
| 5,951,484 A | | 9/1999 | Hoium et al. .............. | 600/515 |
| 6,129,678 A | | 10/2000 | Ryan et al. ................ | 600/515 |
| 6,169,919 B1 | * | 1/2001 | Nearing et al. ............. | 600/518 |
| 6,453,191 B2 | * | 9/2002 | Krishnamachari .......... | 600/515 |
| 6,668,189 B2 | * | 12/2003 | Kaiser et al. ............... | 600/518 |
| 6,735,466 B1 | * | 5/2004 | Haghighi-Mood ......... | 600/515 |
| 6,823,213 B1 | * | 11/2004 | Norris et al. ............... | 607/9 |

OTHER PUBLICATIONS

"T–Wave Alternans: A New Tool For Predicting Arrhythmia and Sudden Cardiac Arrest," Cambridge Heart, Inc., 1999–2000.

"Electrical alternans and cardiac electrical instability," Smith, et al., Diagnostc Methods–Ventricular Arrhythmia, pp. 110–121, vol. 77, No. 1, Jan. 1988.

"Mechanism Linking T–Wave Alternans to the Genesis of Cardiac Fibrillation," Pastore, et al., pp. 1385–1394, Mar. 16, 1999.

"Nonlinear–Dynamical Arrhythmia Control in Humans," Christini, et al., pp. 1–32.

"Intracardiac Detection of T–wave Alternans: Proof of Concept," Christini, et al., pp. 1–9, Oct. 5, 2000; and.

"Using chaos control and tracking to suppress a pathological nonchaotic rhythm in a cardiac model," Christini et al., pp. R49, R51–R52, Physical Review E, vol. 53, No. 1, Jan. 1996.

* cited by examiner

Primary Examiner—Mark Bockelman
(74) Attorney, Agent, or Firm—Darby & Darby

(57) ABSTRACT

Nonlinear-dynamical control, also known as chaos control, can modulate human cardiac electrophysiological dynamics by stabilizing an unstable target rhythm. Intracardiac, repolarization alternans detection methods are disclosed that operates on the basis of amplitude or repolarization duration detection. Also disclosed are control methods for stabilizing repolarization alternans.

21 Claims, 12 Drawing Sheets

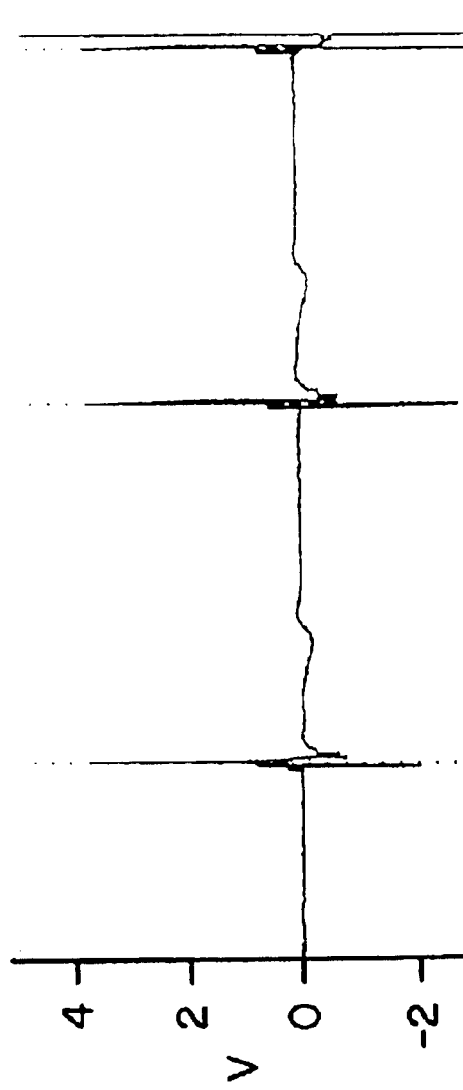
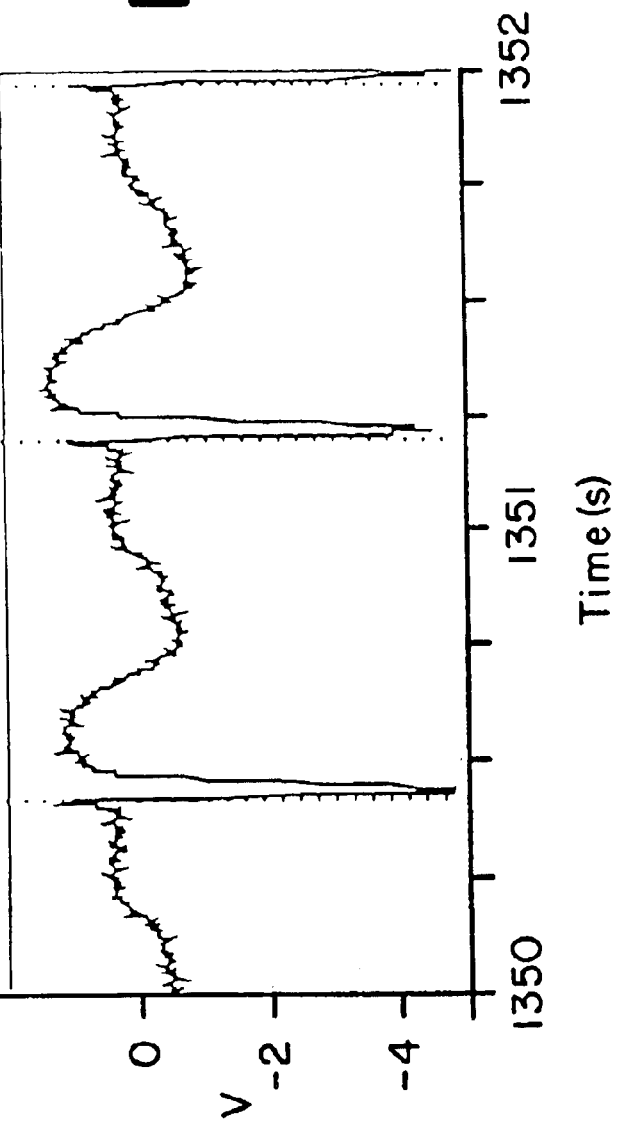
FIG. 2A
FIG. 2B

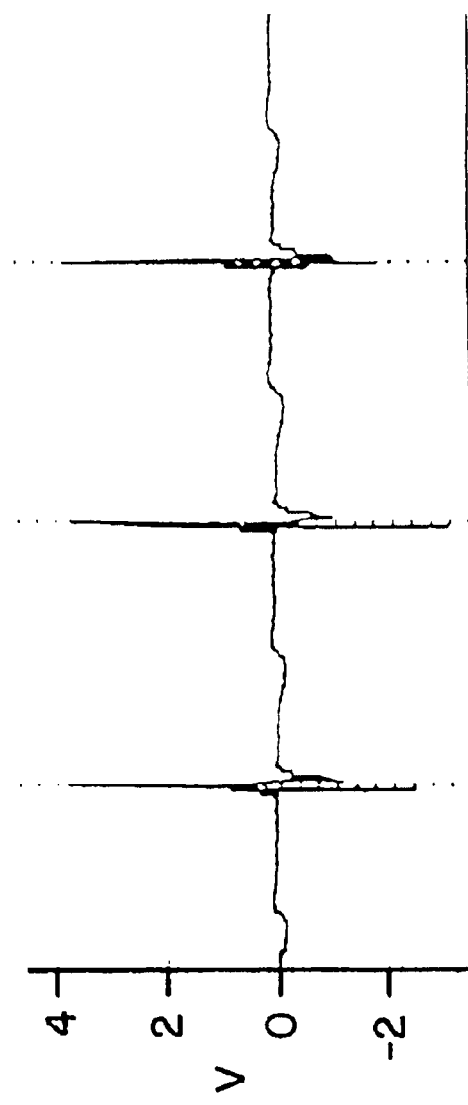
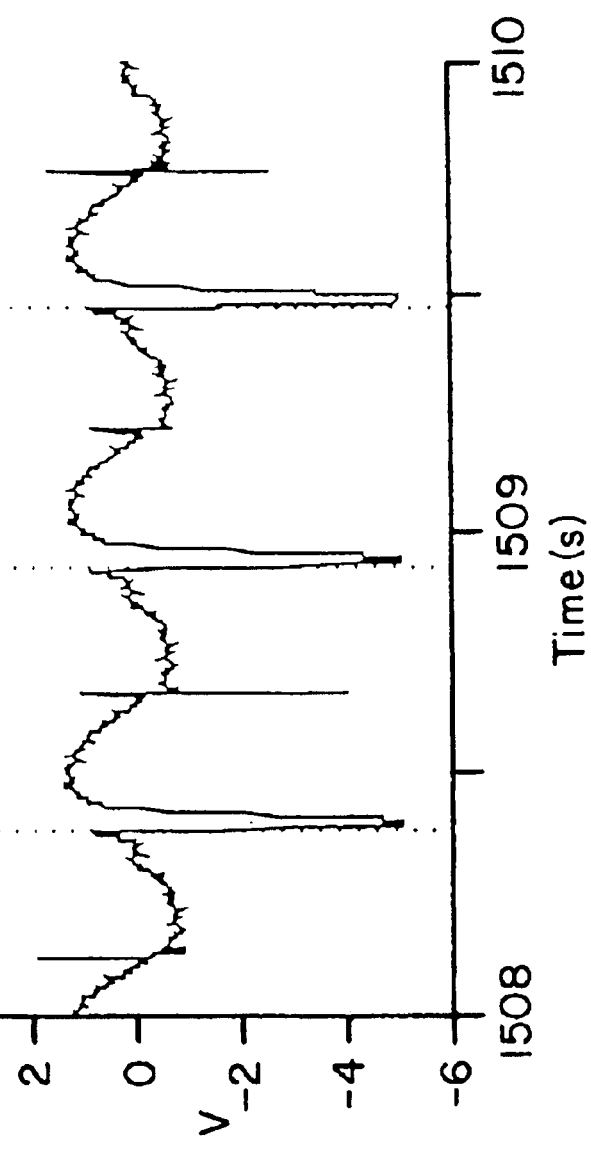
FIG. 3A
FIG. 3B

Time from fiducial pt. (s)

Time from fiducial pt. (s)

FIG. 6
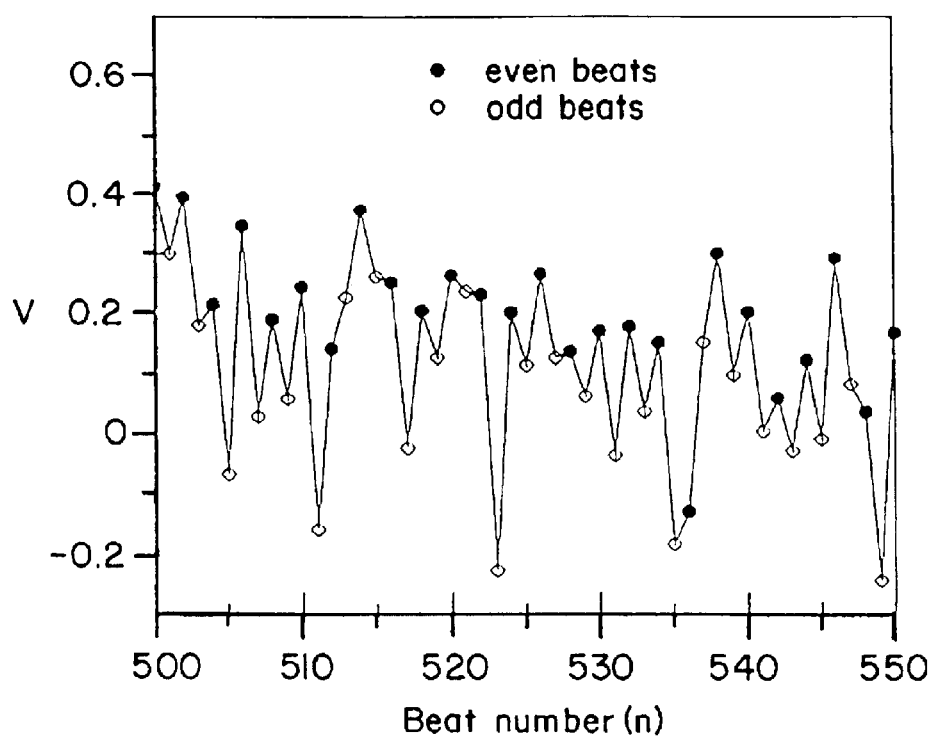
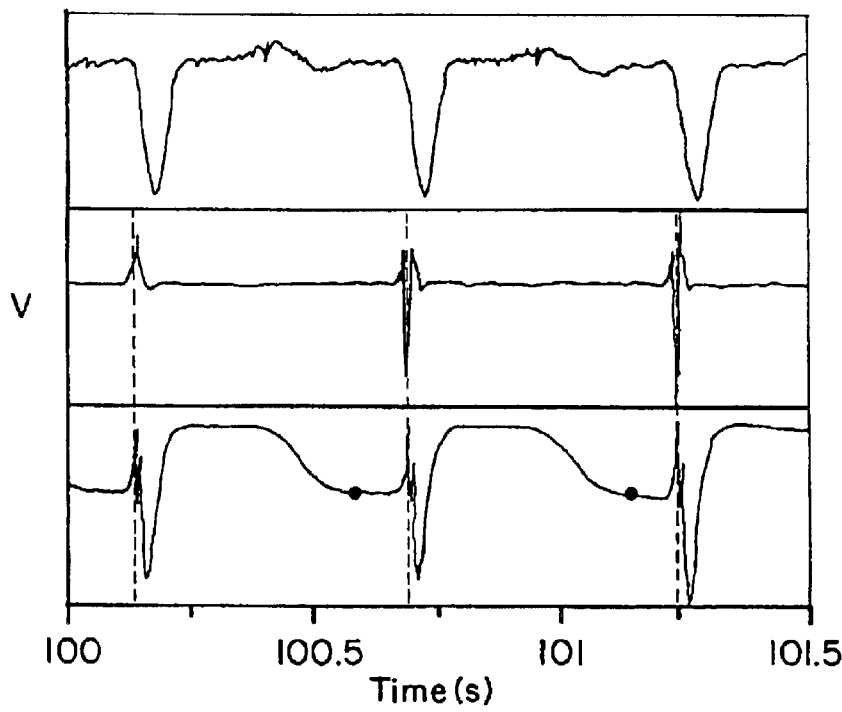
FIG. 8A
FIG. 8B
FIG. 8C

FIG. 7A

| Patient | Gender | Age (years) | Antiarrhythmic medications | Beta-blockers | Cardiac diagnosis | Electrocardiogram | Electrophysiology study indication | Induced MVT | TWA | Endocardial RPA |
|---|---|---|---|---|---|---|---|---|---|---|
| 1 | F | 57 | - | + | NIDCM | LBBB | syncope | - | - | + |
| 2 | F | 27 | - | + | NIDCM | NSRA | syncope | - | + | + |
| 3 | M | 64 | - | + | ICM,CAD | NSRA | NSVT | + | - | + |
| 4 | M | 65 | - | - | NIDCM | LBBB | syncope | - | - | - |
| 5 | M | 32 | - | - | MVP | RVCD, NSRA | CA | - | + | - |
| 6 | M | 51 | - | + | ICM | AWMI, LAFB | NSVT | + | - | - |
| 7 | M | 79 | - | + | ICM | NSRA | syncope | - | - | - |
| 8 | F | 66 | - | - | CAD | IWMI, NSRA | SVT, NSVT | - | - | - |
| 9 | F | 58 | - | - | MR | AWMI | NSVT | - | + | + |
| 10 | M | 68 | - | + | ICM | IVCD, AWMI | NSVT | + | + | + |
| 11 | M | 58 | - | + | ICM | IVCD | NSVT | - | - | + |
| 12 | M | 51 | - | - | ICM | AWMI, NSRA | NSVT | - | + | - |
| 13 | M | 62 | - | - | - | normal | syncope | - | + | + |
| 14 | M | 70 | - | + | ICM | IPMI, ALRA | NSVT | + | + | - |
| 15 | M | 76 | - | + | ICM | 1"AVB, IVCD | NSVT | - | + | + |
| 16 | F | 91 | - | - | CAD, HCM | LVH, ALRA | NSVT, syncope | + | + | - |
| 17 | M | 61 | - | + | ICM | LVH | NSVT | - | - | - |
| 18 | M | 79 | - | + | ICM | 1"AVB, LBBB, AWMI | syncope | - | - | - |
| 19 | M | 75 | Amiodarone | - | CAD | RBBB, LAFB | sustained VT | + | + | - |
| 20 | M | 61 | - | - | ICM | LBBB | sustained VT | - | - | - |
| 21 | M | 36 | - | + | NIDCM | normal | CA | - | - | - |

FIG. 7B

1° AVB: 1st degree atrioventricular-nodal block
ALRA: anterolaterial repolarization abnormalty
AWMI: anterior wall myocardial infarction
CA: cardiac arrest
CAD: coronary artery disease
HCM: hypertrophic cardiomyopathy
ICM: ischemic cardiomyopathy
IPMI: inferoposterior myocardial infarction
IVCD: intraventricular conduction delay
IWMI: inferior wall myocardial infarction
LAFB: left anterior fascicular block
LBBB: left bundle branch block
LVH: left ventricular hypertrophy
MR: mitral regurgitation
MVP: mitral valve prolapse
MVT: monomorphic ventricular tachycardia
NIDCM: non-ischemic dilated cardiomyopathy
NSRA: non-specific repolarization abnormalty
NSVT: non-sustained ventricular tachycardia
RBBB: right bundle branch block
RPA: repolarization alternans
RVCD: right ventricular conduction delay
SVT: supraventricular tachycardia
TWA: T-wave alternans
VT: ventricular techycardia

FIG. 9A

|  | Endocardial RPA | |
|---|---|---|
|  | + | − |
| TWA + | 7 | 4 |
| TWA − | 2 | 8 |

FIG. 9B

|  |  | TWA | | RPA | |
|---|---|---|---|---|---|
|  |  | + | − | + | − |
| MVT | + | 7 | 2 | 5 | 4 |
| MVT | − | 4 | 8 | 4 | 8 |

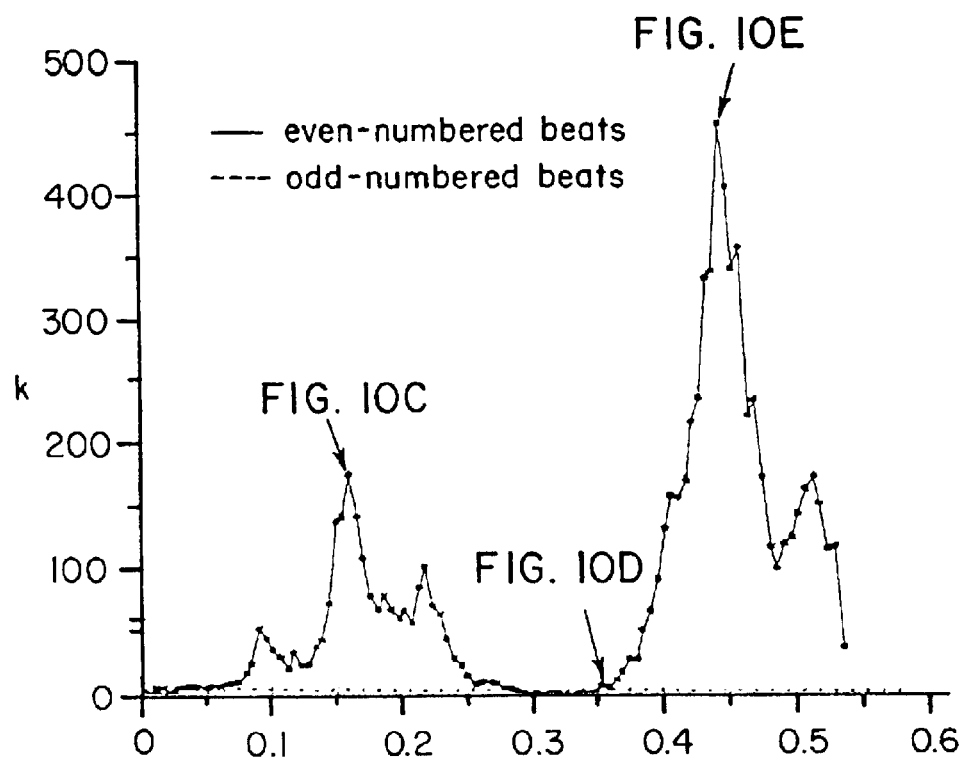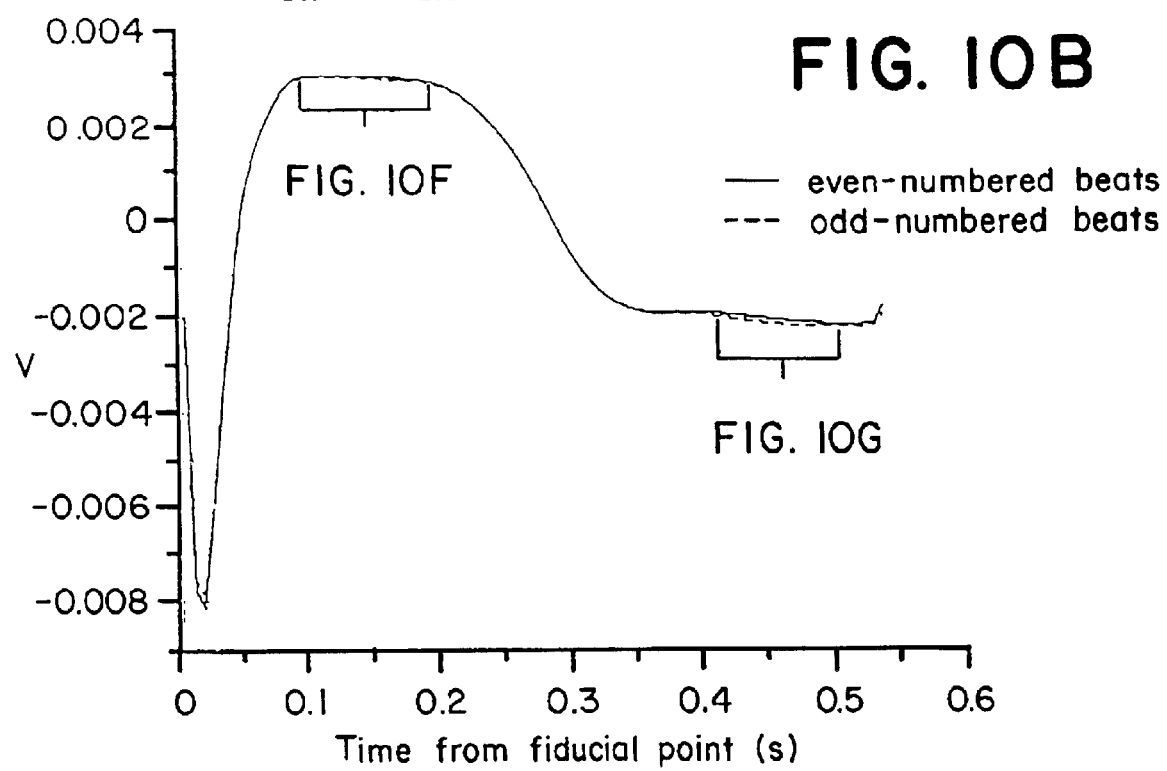

FIG. 10C    FIG. 10D    FIG. 10E
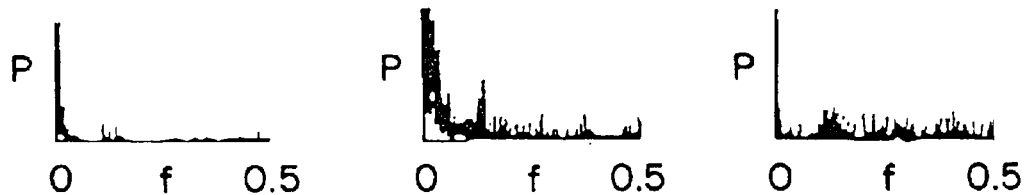
FIG. 10F
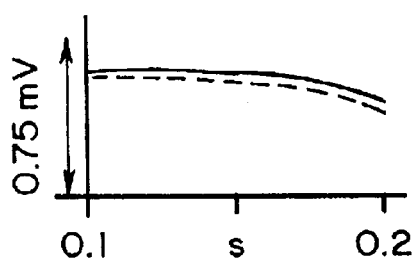
FIG. 10G
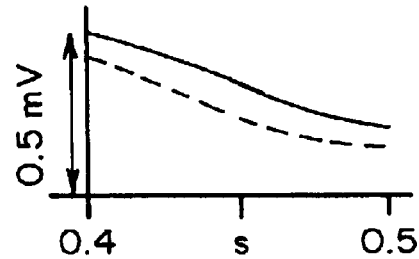
FIG. 12B
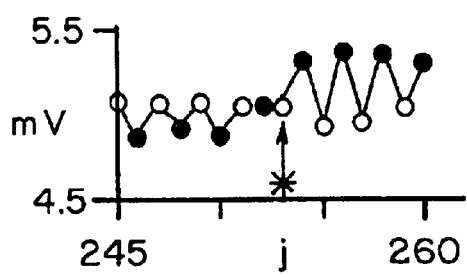
FIG. 12C
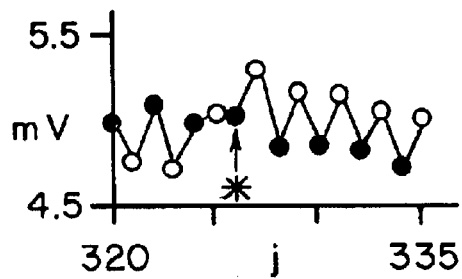
FIG. 12D
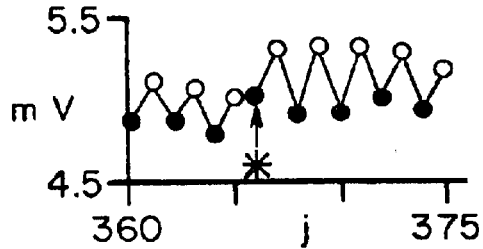
FIG. 11C
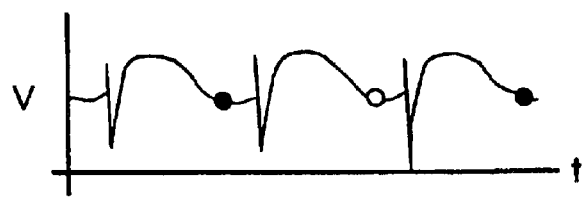

INTRACARDIAC DETECTION AND CONTROL OF REPOLARIZATION ALTERNANS

CROSS-REFERENCE TO THE RELATED APPLICATIONS

This application claims the benefit of priority under 35 U.S.C. §119 from U.S. Provisional Application Ser. No. 60/242,652, filed Oct. 23, 2000, entitled "Intracardiac Detection and Control of Repolarization Alternans," the entirety of which is hereby incorporated by reference.

FIELD OF THE INVENTION

This invention relates to a method and system that can be used to detect and eliminate unwanted dynamics in real-world, low-dimensional dynamical systems. More specifically, this invention relates to a real-time detection technique and a real-time, adaptive, model-independent control technique for detecting and suppressing pathological physiological rhythms, such as repolarization alternans, on the basis of amplitude or repolarization-duration differences among selected beats.

BACKGROUND OF THE INVENTION

It is increasingly recognized that many cardiac arrhythmias can be characterized based on the physical principles of nonlinear dynamics. A nonlinear-dynamical system is one that changes with time (dynamical) and cannot be broken down into a linear sum of its individual components (nonlinear). For certain nonlinear systems, known as chaotic systems, behavior is aperiodic (irregularly irregular) and long-term prediction is impossible, even though the dynamics are entirely deterministic (i.e, the dynamics of the system are completely determined from known inputs and the system's previous state, with no influence from random inputs). Importantly, such determinism can actually be exploited to control the dynamics of a chaotic system. To this end, a variety of chaos-control techniques have been developed and successfully applied to a wide range of physical systems. Such techniques are model-independent, i.e., they require no a priori knowledge of a system's underlying equations, and are therefore appropriate for systems that are essentially "black boxes."

The success of chaos-control techniques in stabilizing physical systems, together with the fact that many physiological systems are nonlinear-dynamical (e.g., the cardiac conduction system, due to its numerous complex nonlinear component interactions) and lack the detailed analytical system models required for model-based control techniques, have fostered widespread interest in applying these model-independent techniques to biological dynamical systems. In the first such application, Garfinkel et al. (A Garfinkel, M L Spano, W L Ditto, and J N Weiss, "Controlling Cardiac Chaos", Science, 257:1230–1235, 1992) stabilized drug-induced irregular cardiac rhythms via dynamically-timed electrical stimulation in an in vitro rabbit ventricular-tissue preparation. That work was an important demonstration that the physical principles of chaos control could be extended into the realm of cardiac dynamics.

A later application is described in U.S. Pat. No. 5,836,974 of Christini et al.

The '974 patent describes a technique in which atrioventricular nodal alternans was controlled by monitoring beat-to-beat timing variations in the atrial-His interval (AH) and then eliminating such variations by making beat-to-beat modifications to a His-atrial pacing interval based on the detected variations in AH time interval.

The present invention concerns repolarization alternans, a beat-to-beat alternation in the manner by which the ventricles of the heart repolarize (i.e., return to resting voltage after their depolarization or excitation). As heart rate or pacing rate increases, action potential duration in different regions of the heart first alternates concordantly and then becomes spatially discordant. Such discordance is associated with steep spatial gradients of repolarization that appear to provide the substrate for unidirectional functional block and reentry. This type of alternans is different than the type detected in the aforesaid '974 patent, because that patent describes a technique which approximates AV node conduction rather than relaxation of the ventricle to return to its original state. The repolarization phase of the heartbeat corresponds to the T-wave component of the surface electrocardiogram (ECG). Thus, repolarization alternans ("RPA"), which to date has always been measured via the surface ECG, is often referred to as T-wave alternans ("TWA"). T-wave alternans appears as a beat-to-beat alternation in the amplitude, morphology, or duration of the T-wave. T-wave alternans has been closely associated with vulnerability to ventricular arrhythmias, including fibrillation. In fact, T-wave alternans can precede life-threatening arrhythmias and is a risk factor for sudden cardiac death.

T-wave alternans, which usually cannot be detected via beat-by-beat visual analysis, is typically detected via statistical analysis of a large number of consecutive surface ECG beats. (Because of the aggregate nature of such detection, detection of T-wave alternans usually requires at least 5 minutes of ECG acquisition.) One known system which utilizes statistical calculations to infer T-Wave alternans from microvolt surface readings is the Cambridge Heart CH2000 system of Cambridge Heart, Inc., Bedford Mass.

What remains needed in the art is a real-time method for detecting and stabilizing repolarization alternans on a beat-to-beat basis.

SUMMARY OF THE INVENTION

Repolarization alternans is detected on a beat-to-beat basis using intracardiac electro grams. The magnitude of such alternans is considerably larger than the microvolt T-wave alternans detected using surface electrodes and so direct measurement of repolarization-phase amplitude differences between even-numbered and odd-numbered heart beats can be measured without the aggregate statistical techniques (such as power spectral analysis) that are required to detect surface microvolt T-wave alternans. Consequently, the present invention permits control stimuli to be delivered in response to real-time alternans data using a suitable nonlinear-dynamical control algorithm.

As an alternative to surface detection of T-wave alternans, repolarization alternans is detected according to the present invention from the inside surface of the heart using intracardiac electrodes, such as those contained in the leads of pacemakers and implantable cardiac defibrillators. Due to the larger intracardiac amplitude, repolarization alterans is discernible (from noise) on a beat-to-beat basis, enabling much more rapid detection than aggregate surface ECG analysis.

Direct detection of repolarization alternans on a beat-to-beat basis enables the application of an adaptive nonlinear-dynamical control technique to control alternating rhythms. This control method delivers precisely-timed electrical stimuli to the cardiac tissue (e.g., ventricular tissue) via intracardiac electrodes. The timing and amplitude of the stimuli (characteristics which are governed by the control algorithm, as dictated by the beat-to-beat dynamics of the repolarization alternans rhythm) is designed to terminate the alternans rhythm. Because the control technique is adaptive, it: (i) is able to estimate the underlying nonlinear dynamics in real time and (ii) has the flexibility to withstand rhythm nonstationarities. With such control, potential routes (repolarization alternans) to a ventricular arrhythmia are eliminated, thereby preventing the onset of a potentially deadly arrhythmic event.

In preferred forms, the control stimuli are delivered by pacemakers or implantable cardiac defibrillators as a component in a preventive therapy.

According to one aspect of the invention, a method for intracardiac detection of repolarization alternans is described which comprises the steps of placing an electrode within the body and within the vicinity of the heart; sensing at the location of the electrode the electrical voltage amplitude at a predetermined time relative to a fiducial point in the heart rhythm of a series of beats, the series of beats including a predetermined number of pairs of adjacent beats, each of the pairs of adjacent beats including an even numbered beat and an odd numbered beat; subtracting the voltage amplitude of an even numbered beat from an odd numbered beat in the adjacent beats, respectively, to obtain for each pair of adjacent beats a sign of the difference in voltage amplitude; and indicating the presence of repolarization alternans if the sign obtained in step (c) for a predetermined number of adjacent pairs of beats is consistent.

According to another aspect of the invention, a method for stabilizing repolarization alternans is described which comprises the steps of contacting at least one electrode to cardiac tissue; sensing at the location of one of the electrodes the electrical voltage amplitude at a predetermined time relative to a fiducial point in the heart rhythm of a series of beats, the series of beats including a predetermined number of pairs of adjacent beats, each of the pairs of adjacent beats including an even numbered beat and an odd numbered beat; subtracting the voltage amplitude of the even numbered beat from the odd numbered beat in at least one pair of adjacent beats to obtain for each said pair of adjacent beats a magnitude of the difference in voltage amplitude and a sign of said difference; dynamically defining an electrical stimuli for delivery to the cardiac tissue, the electrical stimuli including a timing and an amplitude selected in response to the values obtained for the difference in voltage amplitude and the sign of said difference; and conditionally delivering the electrical stimuli to the cardiac tissue if the obtained sign of a predetermined number of adjacent pairs of beats is consistent.

In a further aspect of the invention, a method for intracardiac detection of repolarization alternans is described which comprises the steps of placing an electrode within the body and within the vicinity of the heart; sensing at the location of the electrode a repolarization duration over a segment of a beat in a series of beats, the series of beats including a predetermined number of pairs of adjacent beats, each of the pairs of adjacent beats including an even numbered beat and an odd numbered beat; subtracting the repolarization duration of the even numbered beat from the odd numbered beat in the adjacent beats, respectively, to obtain for each pair of adjacent beats a sign of the difference in repolarization duration; and indicating the presence of repolarization alternans if the sign obtained in step (c) for a predetermined number of adjacent pairs of beats is consistent.

Also, in yet a further aspect of the invention, a method for stabilizing repolarization alternans is described which comprises the steps of: contacting at least one electrode to cardiac tissue; sensing at the location of one of the electrodes a repolarization duration over a segment of a beat in a series of beats, the series of beats including a predetermined number of pairs of adjacent beats, each of the pairs of adjacent beats including an even numbered beat and an odd numbered beat; subtracting the repolarization duration of the even numbered beat from the odd numbered beat in at least one pair of adjacent beats to obtain for each said pair of adjacent beats a magnitude of the difference in repolarization duration and a sign of said difference; dynamically defining an electrical stimuli for delivery to the cardiac tissue, the electrical stimuli including a timing and an amplitude selected in response to the values obtained for the difference in repolarization duration and the sign of said difference; and conditionally delivering the electrical stimuli to the cardiac tissue if the obtained sign of a predetermined number of adjacent pairs of beats is consistent.

BRIEF DESCRIPTION OF THE DRAWINGS

FIGS. 2A and 2B illustrates representative segments of the intracardiac electrograms recorded during the resting stage. The electrogram shown in panel a (FIG. 2A) was recorded from a bipolar electrode at the right ventricular apex. The electrogram shown in panel b (FIG. 2B) was recorded from a unipolar electrode at the right ventricular apex. The dotted vertical lines annotate the fiducial point;

FIGS. 3A and 3B illustrates segments of the intracardiac electrograms recorded during the 550 ms pacing stage. The electrogram shown in panel a (FIG. 3A) was recorded from bipolar electrode at the right ventricular apex. The electrogram shown in panel b (FIG. 3B) was recorded from a unipolar electrode at the right ventricular apex. The dotted vertical lines annotate the fiducial point. The deflections between the fiducial points in panel b (FIG. 3B) are stimulus artifact;

FIG. 6 illustrates the voltage amplitude values that occurred at 0.48 s following fiducial points 500–550 during the pacing stage. There is a distinct alternation between the even numbered (filled circles) and odd numbered (open diamonds) beats, with the even numbered beats typically having larger amplitude than the odd numbered beats.

FIGS. 7A and 7B are tables showing the demographics and results for the patients in a case study that was performed.

FIGS. 8A, 8B and 8C: Representative segments of the electrograms recorded during pacing (550 ms) for Patient 15. (FIG. 8A) surface electrogram, (FIG. 8B) electrogram from a bipolar electrode at the RV apex, and (FIG. 8C) electrogram from a unipolar electrode at the RV apex. The dotted vertical lines annotate the fiducial points as determined from the negative deflections in FIG. 8B.

FIG. 9A relates TWA and RPA to demonstrates that repolarization alternans can be detected from a single spatially-localized endocardial lead.

FIG. 9B relates to the inducibility of monomorphic ventricualr tachycardia to surface TWA and endocardial RPA.

FIG. 10: (A) The k values for each of the 100 slices of the unipolar RV apex recording for Patient 15. The dotted horizontal line is at k=3. There are two large peaks with k >>3 indicating highly significant alternans. The insets, FIGS. 10C, 10D and 10E, (with x-axes in units of cycles/beat and y-axes in unlabeled units of power) show the power spectra for amplitude time series at 0.166, 0.358, and 0.444 s following the fiducial point. The k value corresponding to each inset is indicated by an arrow. As expected, the large k values correspond to power spectra with significant power at 0.5 cycles/beat. (B) The averaged RV apex unipolar voltage amplitudes for the even-numbered beats ($A_{i,j}|_i=1,2,\ldots,100|_j=2,4,6,\ldots,N$; N arbitrarily considered to be even) and odd-numbered beats ($A_{i,j}|_i=1,2,\ldots,100|_j=1,3,5,\ldots,N_{-1}$) during the same trial as shown A. The insets, FIGS. 10F and 10G, show that there is an average amplitude difference between the even- and odd-numbered beats during the same phases of repolarization as the large k peaks in A.

DETAILED DESCRIPTION OF A PREFERRED METHOD

Figure 1:
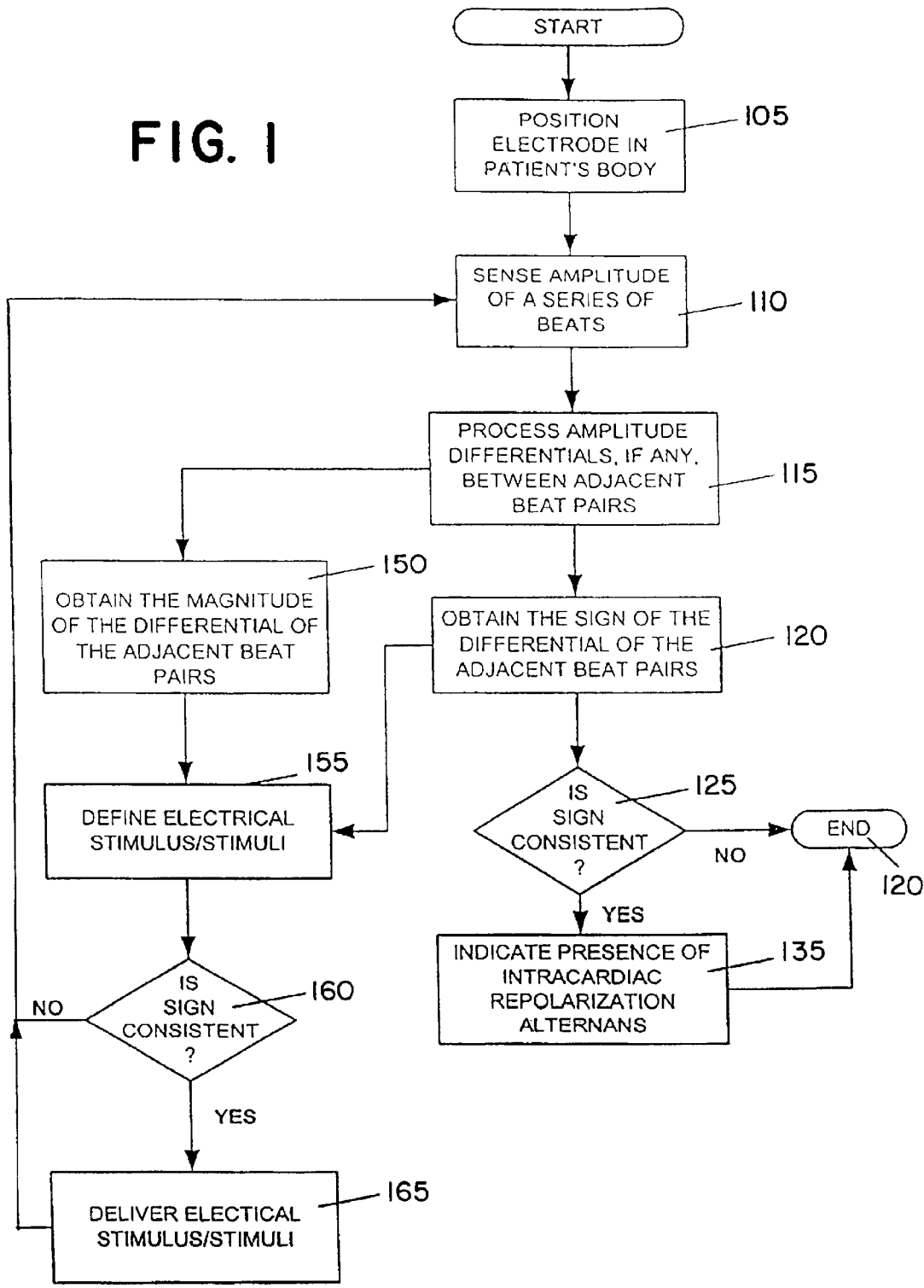
FIG. 1 is a flow chart which outlines an intracardiac repolarization alternans detection procedure in accordance with the invention, as well as a separate procedure for stabilizing intracardiac repolarization alternans.

FIG. 1 is a flow chart which outlines a repolarization alternans detection procedure and also a repolarization alternans stabilization procedure.

The detection method starts at step 105 with one or more electrodes being positioned within a patient's body. The electrodes are preferably connected to a pacemaker or implantable cardiac defibrillator. The construction of the electrode forms no part of the present invention. At step 110, a series of heart beats are sensed by the electrode(s) in any conventional manner at fixed time following a fiducial. The series of beats are processed by dividing them into adjacent beat pairs and then determining the amplitude or repolarization-duration differentials, if any, between the beats of each beat pair, as indicated at step 115. (The "repolarization" refers to the positive deflection in the beat signal, and is the same part of the signal being examined for amplitude.) More particularly, the odd numbered beat in each beat pair can be subtracted from the even number beat in that beat pair, or, conversely, the even numbered beat in each beat pair can be subtracted from the odd number beat in that beat pair. The sign of the difference of the adjacent beat pairs is determined at step 120. If this sign is consistent from one beat pair to an adjacent beat pair, then that is an indicator that there is a repeated repolarization alternation in the patient.

At step 125, the consistency of the sign of this difference in beat-pair to beat-pair magnitude or repolarization-duration is tested. If the sign is not consistent, as tested at step 125, then the detection method ends. Otherwise, if the sign is consistent, then the method indicates to the operator the presence of repolarization alternation, at step 135. The detection method then ends (by looping to step 130).

When the testing of steps 110–135 is performed on the basis of the magnitude of the beat-pair to beat-pair difference, then these steps optionally can be repeated, with each repeat being for a different predetermined time relative to the selected fiducial point in the heart rhythm. By repeating those steps in this way, the presence of alternans can be indicated for any of a number of different parts of the cardiac beat cycle, including portions unrelated to ventricular repolarization. As understood by those of skill in the art, each predetermined time relative to a fiducial point will correspond to a particular part of the cardiac beat cycle.

FIG. 1 also illustrates a methodology for stabilizing repolarization alternans. The stabilization method includes steps 105–120 as outlined above. In addition, the magnitude of the differential between adjacent beat pairs is obtained at step 150 and, together with the sign of the differential (obtained at step 120), is used to define an electrical stimulus or stimuli at step 155 which is selectively applied to an electrode within the vicinity of the heart, and more preferably, an electrode which is engaged to cardiac tissue such as ventricular tissue. The particular electrical stimulus or stimuli that is defined at step 150 will be understood from the following discussion.

At step 160, a test is made to determine consistency in the sign of any beat-pair to beat-pair differential. As was the case at step 125, an arbitrary reference frame is imposed on the beat pairs and either the even numbered beat is subtracted from the odd numbered beat or vice versa in order to arrive at a sign of the difference within a beat and a framework for determining consistency in sign on a beat-pair to beat-pair basis.

If the sign is not consistent, as tested at step 160, then the amplitude of additional beats in a series of heart beats is again detected, as indicated by the arrow looping back to step 110. The heart beat processing is then repeated to dynamically define an electrical stimulus or stimuli to selectively apply through one or more electrodes. Only if the sign is consistent, however, is the electrical stimulus/stimuli delivered to the patient, as indicated at step 165. After delivery of the stimulus, the stabilization method loops back to step 110 so as to process post-stimulus response of the heart and define further electrical stimuli which can differ in magnitude, timing, or both, from any prior stimulus. Consequently, the stabilization method outlined in FIG. 1 modulates human cardiac electrophysiological dynamics in order to stabilize a target rhythm.

In the foregoing steps, electrical stimulus or stimuli are applied to cardiac tissue. It is presently preferred that such stimulus be applied to ventricular tissue insofar as that is the situs of the repolarization alternans. However, such stimuli can be applied elsewhere within the heart using the same type of electrodes (or around the heart by way of a suitable electrode such as a epicardial patch electrode). For example, at least the stimulation electrode(s) can be positioned and discharged (or energized, as the case may be) in the atria. A benefit that may result from placement of the stimulus electrode is a reduced likelihood of the inadvertent inducement of ventricular tachycardia.

An embodiment of the method of the present invention is now described with reference to a case study of an individual patient.

Case Study 1

A 27-year old female patient was evaluated for the presence of repolarization alternans during a clinically-indicated electrophysiology study. Repolarization alternans assessment was performed using: (i) standard surface electrocardiogram (ECG) detection of microvolt T-wave alternans (by the Cambridge Heart CH2000 system) and (ii) intracardiac electrogram acquisition and analysis.

Two distinct stages were studied. The first stage (150 seconds duration) was recorded at rest, i.e., with no electrical pacing. During the second stage (293 seconds duration), the heart was stimulated at a cycle length of 550 ms (109 beats per minute).

Representative segments of the intracardiac electrograms are shown in FIGS. 2A–2B (resting stage) and 3A–3B (550 ms pacing stage). The electrograms shown in FIGS. 2A and 3A are bipolar recordings from an electrode located at the right ventricular apex. The electrograms shown in FIGS. 2B and 3B are unipolar recordings from the right ventricular apex. The unipolar ventricular recording was chosen for alternans detection because its voltage vector covers a greater region of the ventricles than bipolar recordings.

After the electrophysiology study, the electrical depolarizations in the bipolar recording were automatically annotated via a threshold-crossing algorithm (with manual correction as needed). The fiducial point choice and the scheme use to detect it form no part of the present invention; electrophysiologists have a variety of tools at their disposal (e.g., a peak detection system to locate an R-wave peak) to assist them in detecting and selecting an appropriate fiducial point. The occurrence time of each bipolar depolarization was used as the fiducial point for the unipolar amplitude-based repolarization alternans detection algorithm. The analysis, performed separately for the two distinct stages, included the following steps:

1. The occurrence time of each electrical depolarization (in the bipolar recording) was denoted as the beat's fiducial point: $P_0, P_1, \ldots, P_N$, where N is the total number of beats in the stage. Preferably, the occurrence time is determined using a programmed machine, more preferably using a conventional peak detection algorithm. Optionally, manual refinement can be permitted.

2. The minimum inter-depolarization interval T was determined, where T=the minimum of $P_k - P_{k-1}$, for $k=1,2,\ldots, N$.

3. T was subdivided into 100 equally-spaced time slices, $\delta t = T/100$.

4. Starting at each fiducial point, the unipolar voltage values at each time slice are averaged for all beats. For example, for slice #83, which corresponded to the voltage amplitude at 83δt seconds after each fiducial point, the average value was:

$$\frac{1}{N}\sum_{k=0}^{N} V_{Pk} + 83\delta t - V_{Pk} - 0.1.$$

Note that the term $V_{Pk}-0.1$ is the unipolar voltage at a reference point (specifically, the value during the quiescent state 100 ms prior to the fiducial point) that was subtracted to account for long-term drift of the signal. Either if there is no long-term drift or if not desired, then the average value equation can omit the term $V_{Pk}-0.1$.

5. In addition to the overall unipolar aggregate values, the averages were computed separately for odd and even beats.

The results of this case study are as follows. The CH2000 system indicated that there were no microvolt T-wave alternans in the surface electrogram during rest, but that there were microvolt T-wave alternans present in the surface electrogram during the 550 ms pacing stage.

Figure 4:
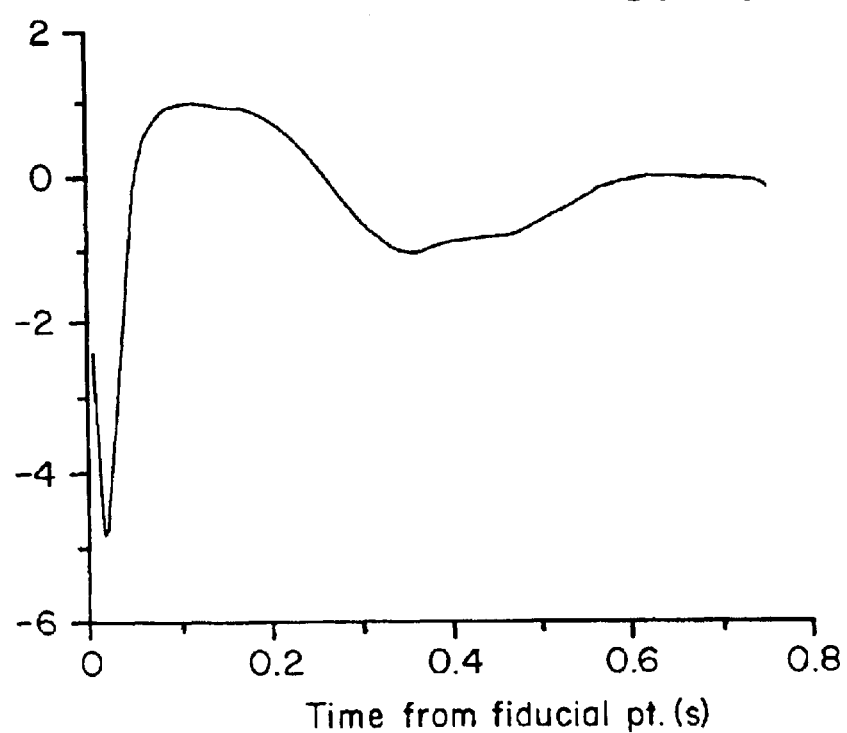
FIG. 4 illustrates the averaged voltage amplitudes for the odd and even beats during the resting stage (two curves are plotted, but because they are nearly identical, they appear as a single curve). The two curves are nearly identical, indicating that, on average, there was no significant difference between the amplitudes of odd numbered and even numbered beats.

FIG. 4 shows the averaged unipolar voltage amplitudes for the odd-numbered and even-numbered beats during the resting stage. The two curves are nearly identical, indicating that, on average, there was no significant difference between the amplitudes of odd and even beats. Thus, as with the CH2000, there was no evidence of repolarization alternans at rest.

Figure 5:
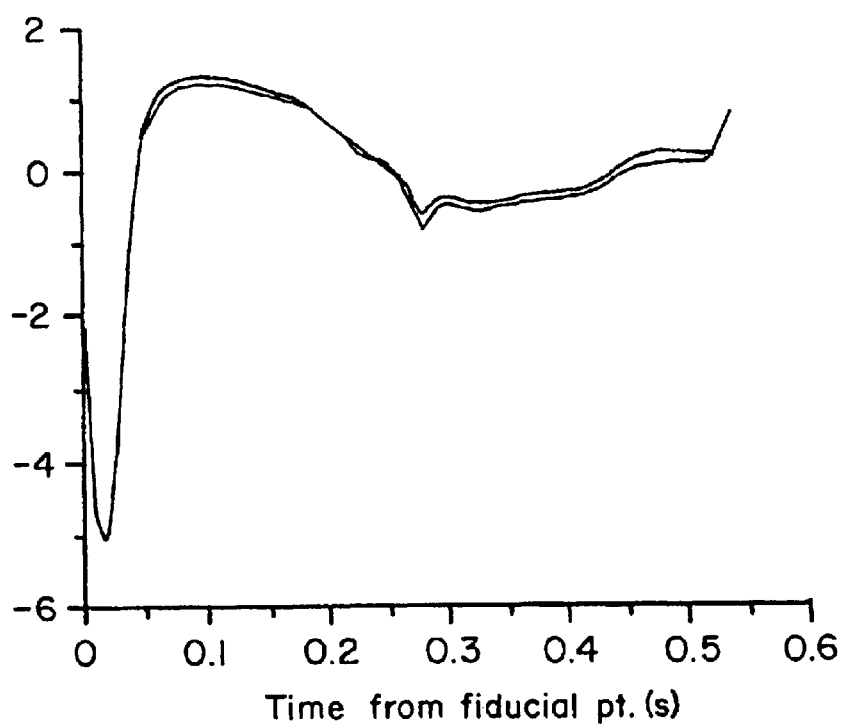
FIG. 5 illustrates the averaged voltage amplitudes for the odd (bottom curve) and even (top curve) beats during the 550 ms pacing stage. There is a clear distinction between the two curves, especially during the latter portion of the beat (at t>0.3 s). The deflection at approximately 0.28 s is the result of the stimulus artifact.

FIG. 5 shows the averaged unipolar voltage amplitudes for the odd-numbered and even-numbered beats during the 550 ms pacing stage. Unlike the resting-stage curves, there is a clear distinction between the two curves. This difference is especially clear during the latter portion of the signal (at t>0.3 s), which coincides with the repolarization stage of the action potential and has been identified as the source of T-wave alternans. This alternation is consistent with the surface T-wave alternans detected by the CH2000 during this stage.

The alternation between even and odd beats can be seen clearly via the beat-to-beat amplitude values at a particular time after the fiducial point.

FIG. 6 shows the voltage amplitude values that occurred 0.48 s following fifty consecutive fiducial points. There is a distinct alternation between the even and odd beats, with the even beats typically having larger amplitude than the odd beats. Notice that an odd beat occasionally has a larger amplitude than the previous or next even beat, but that the dominate alternating pattern always returns within a couple of beats. Also, such outliers do not cause the pattern to invert (i.e., the larger amplitude does not switch to the odd beats). These characteristics imply that the outliers are a result of noise.

An embodiment of the method of the present invention is now described with reference to a case study of multiple patents.

Case Study 2

As a standard component of their routine, clinically-indicated electrophysiological studies, 21 patients (16M, 5F; 62±16yr) were evaluated for the presence of repolarization alternans (See the table in FIGS. 7A and 7B for patient demographics). The electrophysiologic studies were performed using standard techniques, which included the introduction of three percutaneous catheters (6F quadripolar catheters with 5-mm interelectrode spacing; Bard EP, Billerica, Mass.) from the femoral veins to pace and record endocardial signals from the right atrium, His-bundle region, and right ventricle (RV). Electrophysiological testing used:

(i) single, double, and triple ventricular extrastimuli at two drive cycles from two right ventricular sites and from one right ventricular site during isoproterenol or dobutamine infusion, and (ii) rapid ventricular pacing. Inducibility of monomorphic ventricular tachycardia required uniform twelve-lead tachycardia morphology, regardless of cycle length, lasting $\geq 30$ s or requiring termination due to hemodynamic compromise.

For TWA assessment, careful skin preparation (including mild abrasion) and high resolution electrodes (High-Res, Cambridge Heart, Inc., Bedford, Mass.) were used to minimize noise. Electrocardiographic leads were placed at the standard 12-lead positions and in an orthogonal X,Y,Z configuration. Measurement was performed using the CH2000 (patients 1–10) or HearTwave (patients 11–21) system (both systems are from Cambridge Heart, Inc.) during 5 min of atrial pacing at a cycle length of 550 ms (109 beats/min). A trial was considered positive for surface TWA if the alternans amplitude was $\geq 1.9$ $\mu$V and the alternans ratio $\geq 3$ for at least one min in the vector magnitude lead, any orthogonal lead, or two consecutive precordial leads. T-wave alternans was defined as negative if the tracing was not obscured by noise or ectopic beats (both of which can lead to under-detection of TWA) and the criteria for a positive test were not met. Otherwise, the TWA test was considered indeterminate (i.e., due to noise or ectopy).

Indeterminate results are not included in this study because of the inability to compare surface TWA and endocardial RPA results. Eight patients that satisfied the protocol (and who are omitted from the 21 patients described here) were omitted for this reason.

Simultaneously, for the purpose of endocardial RPA assessment, three signals (surface electrogram, bipolar RV apex, and unipolar RV apex) were sampled at 500 Hz by a National Instruments AT-MIO-16E-10 (National Instruments Corporation, Austin, Tex.) data acquisition board in a 266 MHz Intel Pentium-II powered computer running Real-Time Linux through a user interface. Representative segments of these electrograms from one patient are shown in FIGS. 8A, 8B and 8C.

After the electrophysiologic study, the bipolar RV apex recording was automatically annotated via a peak-detection algorithm (with manual correction as needed) using custom C++ software in order to determine the occurrence time of each electrical depolarization. The activation time of each bipolar depolarization was used as the fiducial point for an amplitude-based repolarization alternans detection algorithm. The bipolar RV apex signal was selected for fiducial point determination because of its sharply defined peaks. The unipolar RV apex recording was used for alternans measurement because repolarization alternans results from a spatially extended dispersion of ventricular repolarization and because the unipolar voltage vector covers a greater area of ventricular myocardium than standard bipolar recordings. The construction of the unipolar amplitude time series consisted of the following steps:

1. The occurrence time of each RV apex bipolar depolarization was denoted as the beat's fiducial point, $R_1$, $R_2$, . . . , $R_N$, where N is the total number of beats in the 5 min trial.
2. The minimum inter-depolarization interval T was determined (excluding ectopic intervals that were less than 90% of the mean interval which are instead handled in step 4(b) below), where T=the minimum of $(R_j-R_{j-1})$, for j=1,2, . . . , N. In general, T=the paced cycle length of 550 ms.
3. T was subdivided into 100 equally-spaced time slices, $\delta t = T/100$.
4(a). Starting at each fiducial point, the unipolar voltage values at each time slice were averaged for all beats. This entails constructing a prescribed number (e.g., 100) of time series $A_{i,j}$ each having N amplitude values by sampling the unipolar RV apex signal at equally-spaced times $\delta t$ between each fiducial point:

$$A_{i,j} = V(R_j + i\delta t) | i=1,2, \ldots, 100 |, j=1,2 \ldots, N \qquad (1)$$

where V(t) is the voltage of the unipolar RV apex recording at time t for the prescribed number (here, 100) of time series, and i is a series from particular slice of time.

Graphically, two elements of an $A_{i,j}$ time series are shown in FIG. 8C as closed circles that mark the voltage values for $A_{82,j}$ and $A_{82,j+1}$, where the $82^{nd}$ slice corresponds to the time 0.444 s after the preceding fiducial point. The complete $A_{82,j}$ time series would be comprised of such points from every beat (j=1,2, . . . , N) in the time series.

4(b). In the case of an exception, as noted above in step 2, then at least $j^{th}$ beat was ectopic (i.e., $R_j-R_{j-1}$ was less than 90% of the mean interval), $A_{i,j}$ and $A_{i,j-1}$ were replaced by the average values from all previous beats:

$$A_{i,j-1} = \frac{1}{j-2} \sum_{m=1}^{j-2} A_{i,m}, \qquad (2)$$

$$A_{i,j} = A_{i,j-1}. \qquad (3)$$

5. In addition to the overall unipolar aggregate values, the averages were computed separately for odd and even beats.

The results of this case study are as follows. In the results, the power spectral densities were computed for each of the $A_{i,j}$ 100 time series using the FFTW C-library implementation of the Cooley-Tukey Fast Fourier Transform (www.fftw.org). In addition to being computationally efficient, the FFTW implementation is convenient because it is applicable to arbitrary-length time series. Thus, time series that incorporate data from every beat of a 5 min pacing trial could be processed directly without the standard conversion to a power-of-2 length time series. A peak at 0.5 cycles/beat is indicative of alternans. To establish significance, the ratio k of alternans power (minus mean noise power) to noise standard deviation was computed for each slice:

$$k = \frac{P_{0.5} - \overline{P}_{0.44 \to 0.49}}{\sigma_{0.44 \to 0.49}} \qquad (4)$$

where is $P_{0.5}$ is the power at 0.5 cycles/beat, $\overline{P}_{0.44 \to 0.49}$ and $\sigma_{0.44 \to 0.49}$ are the mean and standard deviation, respectively, of the power for all of the frequencies in the band 0.44 cycles/beat to 0.49 cycles/beat. RPA is significant ($\rho \leq 0.003$) if k>3. For this study, a trial was considered positive for endocardial RPA if k>3 for 10 consecutive time slices, which is equivalent to $\approx 0.055$ s given that each 550 ms pacing interval was subdivided into 100 time slices.

As shown in FIG. 9A, there was a 71% concordance (15/21; kappa=0.432, p=0.04) between surface TWA and endocardial RPA: 7/21 patients had TWA and endocardial RPA, while 8/21 patients had neither. These results show that it is, in fact, possible to detect repolarization alternans from a single spatially-localized endocardial lead in humans. Also, as shown in FIG. 9B, there was a high concordance between inducibility of monomorphic ventricular tachycardia and the presence of surface TWA (15/21; 71%; kappa=0.432, p=0.04) and endocardial RPA (13/21; 62%; kappa=0.222, p=NS). These results, although not statistically significant, suggest that endocardial RPA detection is similar to surface TWA detection for prediction of inducibility of ventricular tachycardia.

A representative positive endocardial RPA trial is shown in FIGS. 10A and 10B. Panel A (FIG. 10A) shows the k values for each of the 100 slices of the unipolar RV apex recording that as shown in part in FIG. 8C. There are two large peaks with k>>3 indicating highly significant alternans. The three insets (FIGS. 10C, 10D and 10E) show the power spectra from which three corresponding k values (indicated by arrows) were computed. As expected, the large k values correspond to power spectra with significant power at 0.5 cycles/beat.

The power-spectral analyses depicted in FIG. 10A are a measure of the aggregate properties of the RPA time series. Another method of visualizing such aggregate properties is shown in FIG. 10(B). This figure shows the averaged RV apex unipolar voltage amplitudes for the even-numbered beats ($A_{i,j}|_i=1,2,\ldots,100|_j=2,4,6,\ldots,N$; N arbitrarily considered to be even) and odd-numbered beats ($A_{i,j}|_i=1,2,\ldots,100|_j=1,3,5,\ldots,N-1$) during the 550 ms pacing phase for the same trial as that of FIG. 10(A). There is an amplitude difference between the averaged even- and odd-numbered beats that correspond to the same phases of repolarization as the large κ peaks in FIG. 10(A).

Figure 11A:
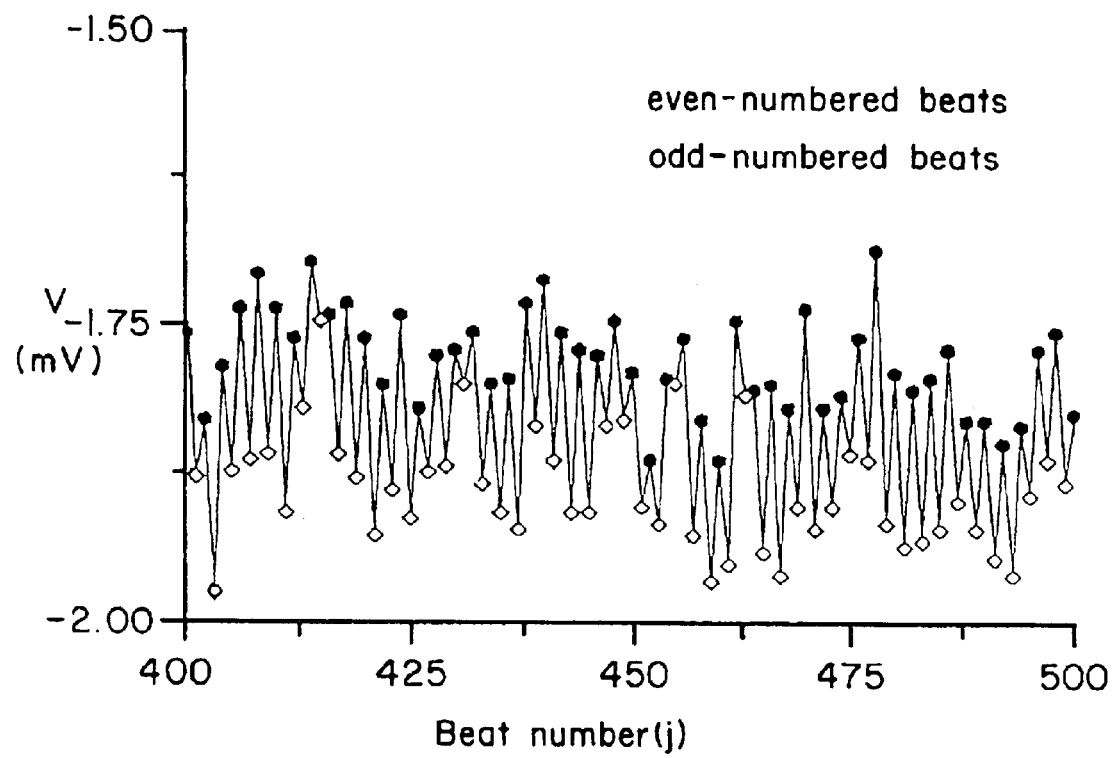
FIG. 11: (A) The endocardial unipolar RV apex voltage amplitude values $A_{i,j}$ that occurred 0.444 s (i=82) following fiducial points $400 \leq j \leq 500$ for Patient 15. There is a distinct alternation between the even (filled circles) and odd (open diamonds) beats, with the even beats typically having larger amplitude than the odd beats. The inset.
FIG. 11C, shows three consecutive beats with annotations corresponding to the voltage values at 0.444 s following the fiducial point (fiducial point not marked). (B) The histogram of successive-beat amplitude differences $\Delta A_i = A_{i,j+1} - A_{i,j}$ for j=1,2, . . . , N is shown for i=82. The solid curve is a nonlinear regression fit to the histogram values.

In 6/8 in which power spectral analysis indicated the presence of endocardial RPA (FIG. 9A), the maximum k value was >20. In all 6 of those trials, RPA was visually apparent on a beat-to-beat basis. FIG. 11(A) (which is from the same trial as FIG. 10A and B) shows the amplitude values $A_{i,j}$ of 100 successive beats at the time slice 0.444 s (i =82) after the fiducial point 12A shows for a segment during which three ectopic beats occurred. The first two topic beats reversed the phase of the alternation, while the third ectopic beat had no effect on th phase. Out of all five ectopic beats that occurred during the trial, three reversed the phase. All three phase reversals occurred when the ectopic beat followed the lower-amplitude value of the alternating phase, while the two ectopic beats that did not reverse the phase followed the higher-amplitude value of the alternating phase. Note that phase reversal was independent of the substitution of averaged values and unchanged when the analysis was repeated without substitution.

Figure 11B:
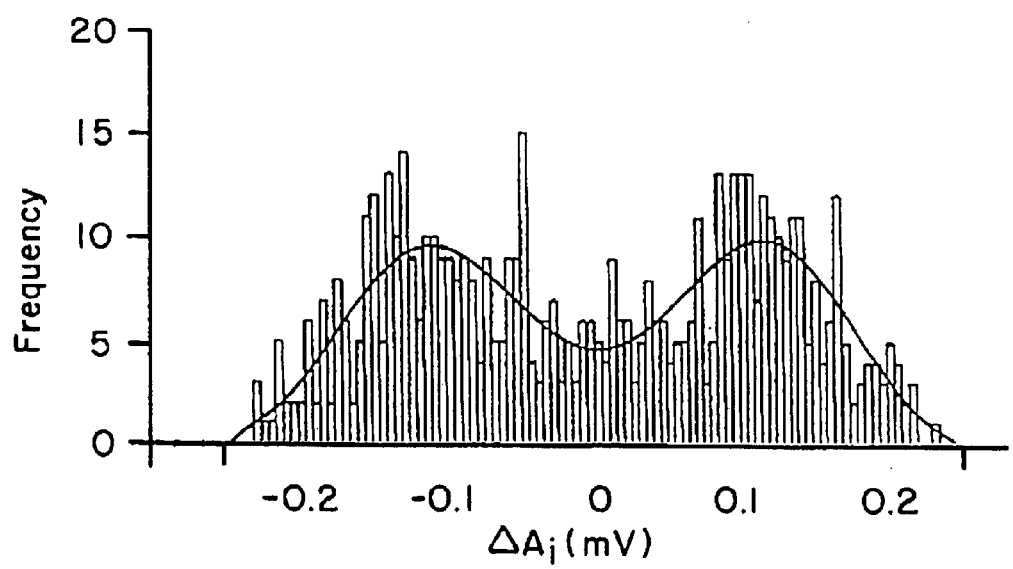

This alternating pattern persisted for the entire 5 min pacing trial, leading to an average even-numbered amplitude minus subsequent odd-numbered amplitude $$\left(\frac{2}{N}\sum_{m}^{N}=2,4,6\ldots A_{i,m}-A_{i,m-1}\right)$$

of −0.104 mV and an average odd-numbered amplitude minus subsequent even-numbered amplitude $$\left(\frac{2}{N}\sum_{m=1,3,5\ldots}^{N-1}A_{i,m}-A_{1,m-1}\right)$$

of 0.098 mV. This alternating pattern is also apparent when the successive-beat amplitude differences $\Delta A_i = A_{i,j}+1-A_{i,j}$ for $j=1,2,\ldots,N$ are plotted as a histogram. The histogram of successive-beat amplitude differences for i=82, shown in FIG. 11(B), has a clear bi-modal distribution centered at 0.0 mV with two peaks at approximately ±0.1 mV.

Figure 12A:
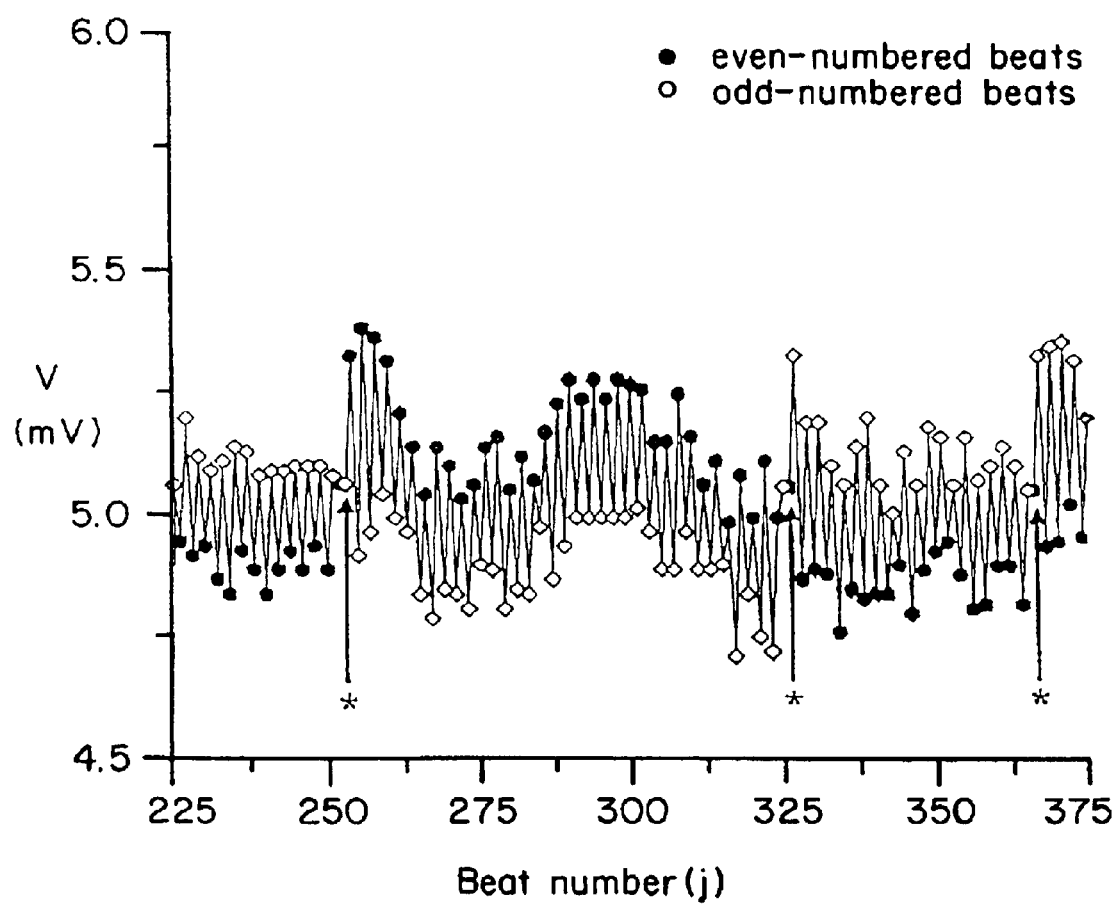
FIG. 12A: The endocardial unipolar RV apex voltage amplitude values $A_{i,j}$ that occurred 0.064 s (i=11) following fiducial points $225 \leq j \leq 375$ for Patient 13. During this segment, three ectopic beats occurred at the beats indicated by "*". The amplitude values for the ectopic beat an the preceding beat were replaced by the average values from all previous beats as described above. The beats before and after each ectopic beat are magnified in an inset, FIGS. 12B, 12C and 12D. The first two ectopic beats reversed the phase of the alternation, while the third ectopic beat had no effect on the phase.

Occasionally ectopic beats reversed the phase of the beat-to-beat alternans. FIG. 12 shows for a segment during which three ectopic beats occurred. The first two ectopic beats reversed the phase of the alternation, while the third ectopic beat had no effect on the phase. Out of all five ectopic beats that occurred during the trial, three reversed the phase. All three phase reversals occurred when the ectopic beat followed the lower-amplitude value of the alternating phase, while the two ectopic beats that did not reverse the phase followed the higher-amplitude value of the alternating phase. Note that phase reversal was independent of the substitution of averaged values and unchanged when the analysis was repeated without substitution.

The Control Technique

Once alternans has been detected, an adaptive chaos-control technique can be used to terminate the alternans. Repolarization alternans is not believed to be a chaotic rhythm; however, the control technique described herein to terminate repolarization alternans is a chaos-control technique.

The control algorithm used herein is designed to stabilize the underlying unstable steady state x* of a system that can be described by a unimodal one-dimensional function $^x n+1 = f(x_n, p_n)$, where $x_n$ is the current value of the system variable of interest x (for repolarization alternans, x is the amplitude, A, of the repolarization phase of the intracardiac electrogram), $^x n+1$ is the next value of the same variable, and $p_n$ is the current value of an accessible system parameter p (for repolarization alternans control, p can be the timing and/or the amplitude of electrical stimuli) at index n. Thus, for repolarization alternans, the system function is $$A_{n+1} = f(A_n, p_n), \quad (5)$$

where n is the beat number. The control technique perturbs p such that $$p_n = \bar{p} + \delta p_n, \quad (6)$$

where $\bar{p}$ is the nominal parameter (stimulus timing and/or amplitude) value, and $\delta p_n$, is a perturbation given by $$\delta p_n = (A_n - A_{n-1})/g_n \quad (7)$$

where $g_n$ is the control sensitivity g at index n. Thus, for each electrical stimulus, the chaos-control algorithm computes a perturbation (proportional to the difference between the most recent two repolarization phase amplitudes) to the nominal stimulus amplitude and/or timing. Note that if both stimulus amplitude and timing are used as adjustable control parameters, separate realizations of Equations 5–7 would be used, including separate g values.

The control sensitivity g is adaptively estimated at each beat, thereby providing inherent algorithmic dynamic flexibility. g is adapted in real-time based on the characteristic dynamics of unimodal one-dimensional systems. Specifically, for every beat, if the sign of the computed perturbation (Eq. 7) has alternated for the four previous perturbations, the magnitude of g is decreased by a factor r (for this study r=0.05), otherwise, the magnitude g of is increased by a factor r.

This chaos-control technique requires no pre-control learning stage and is robust to dynamical system changes because it estimates the control parameters and target-rhythm dynamics in real-time. Thus, it is capable of applying control immediately upon the detection of an arrhythmia and is able to maintain control as the dynamics of the arrhythmia change over time.

The terms "even" and "odd" as used herein with regard to heart beats are arbitrary. An even numbered beat can be an odd numbered beat, and vice versa, simply by shifting the reference point by one beat. What is important is that measurements made with regard to adjacent pairs of beats are made by consistently subtracting either odd numbered beats from even numbered beats, or vice versa.

The term "sign" is used in this specification in its mathematical sense to refer to the positive or negative nature of the difference obtained when processing the even and odd numbered heart beats.

The invention can include delivery of electrical stimuli at a plurality of locations rather than just one, and energy delivery can be performed serially, simultaneously or otherwise at these locations. Each electrode can be driven in accordance with its own set of driving equations. The foregoing discussion explains by way of example driving equations for any given electrode.

The invention has been described in connection with a particular embodiment but is defined without limitation by the claims appended hereto and includes insubstantial variations in elements and method steps.

We claim:

1. A method for intracardiac detection of repolarization alternans, comprising the steps of:
   a) placing an electrode within the body and within the vicinity of the heart;
   b) sensing at the location of the electrode the electrical voltage amplitude at a predetermined time relative to a fiducial point in the heart rhythm of a series of beats, the series of beats including a predetermined number of pairs of adjacent beats, each of the pairs of adjacent beats including an even numbered beat and an odd numbered beat;
   c) subtracting the voltage amplitude of the even numbered beat from the odd numbered beat in the adjacent beats, respectively, to obtain for each pair of adjacent beats a sign of the difference in voltage amplitude; and
   d) indicating the presence of repolarization alternans if the sign obtained in step (c) for a predetermined number of adjacent pairs of beats is consistent.

2. The method as in claim 1, wherein the electrode placement step comprises contacting the electrode to cardiac tissue.

3. The method as in claim 1, wherein the electrode placement step comprises implanting the electrode into cardiac tissue.

4. The method as in claim 1, wherein the predetermined time relative to a fiducial point occurs during the ventricular repolarization phase of the cardiac cycle.

5. The method as in claim 1, wherein steps (b) through (d) are repeated multiple different predetermined times relative to the fiducial point in the heart rhythm, whereby the detection method indicates the presence of repolarization alternans at any of a number of different parts of the cardiac beat cycle corresponding to said the multiple different predetermined times.

6. A method for stabilizing repolarization alternans, comprising the steps of:
   a) contacting at least one electrode to cardiac tissue;
   b) sensing at the location of one of the electrodes the electrical voltage amplitude at a predetermined time relative to a fiducial point in the heart rhythm of a series of beats, the series of beats including a predetermined number of pairs of adjacent beats, each of the pairs of adjacent beats including an even numbered beat and an odd numbered beat;
   c) subtracting the voltage amplitude of the even numbered beat from the odd numbered beat in at least one pair of adjacent beats to obtain for each said pair of adjacent beats a magnitude of the difference in voltage amplitude and a sign of said difference;
   d) dynamically defining an electrical stimuli for delivery to the cardiac tissue, the electrical stimuli including a timing and an amplitude selected in response to the values obtained for the difference in voltage amplitude and the sign of said difference;
   e) conditionally delivering the electrical stimuli to the cardiac tissue if the obtained sign of a predetermined number of adjacent pairs of beats is consistent.

7. The method as in claim 6, including the additional step of repeating steps (b) through (e).

8. The method as in claim 6, including the additional step of repeating steps (b) through (e) a multiplicity of times to minimize the difference in voltage amplitude between adjacent beats.

9. The method as in claim 6, wherein the sensing and delivering steps utilize the same electrode.

10. The method as in claim 6, wherein the sensing step comprises sensing the series of beats at a plurality of locations.

11. The method as in claim 6, wherein the delivery step comprises delivering the electrical stimuli to the cardiac tissue at a plurality of locations.

12. The method as in claim 6, wherein the predetermined time relative to a fiducial point occurs during the ventricular repolarization phase of the cardiac cycle.

13. A method for intracardiac detection of repolarization alternans, comprising the steps of:
   a) placing an electrode within the body and within the vicinity of the heart;
   b) sensing at the location of the electrode a repolarization duration over a segment of a beat in a series of beats, the series of beats including a predetermined number of pairs of adjacent beats, each of the pairs of adjacent beats including an even numbered beat and an odd numbered beat;
   c) subtracting the repolarization duration of the even numbered beat from the odd numbered beat in the adjacent beats, respectively, to obtain for each pair of adjacent beats a sign of the difference in repolarization duration; and
   d) indicating the presence of repolarization alternans if the sign obtained in step (c) for a predetermined number of adjacent pairs of beats is consistent.

14. The method as in claim 13, wherein the electrode placement step comprises contacting the electrode to cardiac tissue.

15. The method as in claim 13, wherein the electrode placement step comprises implanting the electrode into cardiac tissue.

16. A method for stabilizing repolarization alternans, comprising the steps of:
   a) contacting at least one electrode to cardiac tissue;
   b) sensing at the location of one of the electrodes a repolarization duration over a segment of a beat in a series of beats, the series of beats including a predetermined number of pairs of adjacent beats, each of the pairs of adjacent beats including an even numbered beat and an odd numbered beat;
   c) subtracting the repolarization duration of the even numbered beat from the odd numbered beat in at least one pair of adjacent beats to obtain for each said pair of adjacent beats a magnitude of the difference in repolarization duration and a sign of said difference;

d) dynamically defining an electrical stimuli for delivery to the cardiac tissue, the electrical stimuli including a timing and an amplitude selected in response to the values obtained for the difference in repolarization duration and the sign of said difference;

e) conditionally delivering the electrical stimuli to the cardiac tissue if the obtained sign of a predetermined number of adjacent pairs of beats is consistent.

17. The method as in claim 16, including the additional step of repeating steps (b) through (e).

18. The method as in claim 16, including the additional step of repeating steps (b) through (e) a multiplicity of times to minimize the difference in repolarization duration between adjacent beats.

19. The method as in claim 16, wherein the sensing and delivering steps utilize the same electrode.

20. The method as in claim 16, wherein the sensing step comprises sensing the series of beats at a plurality of locations.

21. The method as in claim 16, wherein the delivery step comprises delivering th e electrical stimuli to the cardiac tissue at a plurality of locations.

* * * * *